(12) United States Patent
Aldalbahi et al.

(10) Patent No.: US 10,689,257 B1
(45) Date of Patent: Jun. 23, 2020

(54) BIO BUCKYPAPER SYNTHESIZED WITH FISH SCALES

(71) Applicant: KING SAUD UNIVERSITY, Riyadh (SA)

(72) Inventors: Ali Kanakhir Aldalbahi, Riyadh (SA); Manal Ahmed Gasmelseed Awad, Riyadh (SA); Khalid Mustafa Osman Ortashi, Riyadh (SA); Shaykha Mohammed Alzahly, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/383,356

(22) Filed: Apr. 12, 2019

(51) Int. Cl.
| | |
|---|---|
| *D21F 13/00* | (2006.01) |
| *D21H 13/50* | (2006.01) |
| *B29C 67/00* | (2017.01) |
| *B82Y 40/00* | (2011.01) |
| *C01B 32/16* | (2017.01) |
| *C01B 32/174* | (2017.01) |
| *B82Y 30/00* | (2011.01) |

(52) U.S. Cl.
CPC .............. *C01B 32/16* (2017.08); *B29C 67/00* (2013.01); *C01B 32/174* (2017.08); *D21F 13/00* (2013.01); *D21H 13/50* (2013.01); *B82Y 30/00* (2013.01); *B82Y 40/00* (2013.01); *C01B 2202/04* (2013.01); *C01B 2202/06* (2013.01)

(58) Field of Classification Search
CPC ..... C01B 32/16; C01B 32/174; C01B 32/158; C01B 32/159; C01B 32/166; B82Y 30/00; B82Y 40/00; B01D 71/021; D21H 13/50; D21F 13/00; B29C 67/0011

USPC ........ 162/178, 143, 148, 151; 977/742, 750, 977/752, 753
See application file for complete search history.

(56) References Cited

U.S. PATENT DOCUMENTS

| | | |
|---|---|---|
| 9,926,201 B1 | 3/2018 | Kessler |
| 2008/0128659 A1 | 6/2008 | Parker |

FOREIGN PATENT DOCUMENTS

| | | |
|---|---|---|
| KR | 20150018958 A | 2/2015 |
| KR | 20170090604 A | 8/2017 |

OTHER PUBLICATIONS

Aldalbahi, Ali, "Nano-composite materials from carrageenan, conducting polymers and carbon nanotubes," Doctor of Philosophy Thesis, School of Chemistry, University of Wollongong. (Year: 2012).*

Haug et al., Physical behaviour of fish gelatin-kappa-carrageenan mixtures, Carbohydrate Polymers 56, pp. 11-19. (Year: 2004).*

(Continued)

*Primary Examiner* — Eric Hug
(74) *Attorney, Agent, or Firm* — Richard C. Litman; Nath, Goldberg & Meyer (57) ABSTRACT

A bio buckypaper synthesized with fish scales may be manufactured by mixing carrageenan with a bio waste solution to provide a first mixture, adding carbon nanotubes to the first mixture produce a second mixture, sonicating the second mixture, and evaporative-casting the second mixture to produce the bio buckypaper. In an embodiment, the carrageenan may be τ-carrageenan. In an embodiment, the carbon nanotubes may be single walled carbon nanotubes (SWCNTs) or multi-walled carbon nanotubes (MWCNTs). In an embodiment, the bio waste solution may be derived from fish scales.

9 Claims, 14 Drawing Sheets

(56) References Cited

OTHER PUBLICATIONS

Alshahrani et al., "Synthesis and characterisation of MWNT/chitosan and MWNT/chitosan-crosslinked buckypaper membranes for desalination," Desalination, vol. 418, Sep. 15, 2017, pp. 60-70.
Aldalbahi, A. and Panhuis, M., "Electrical and mechanical characteristics of buckypapers and evaporative cast films prepared using single and multi-walled carbon nanotubes and the biopolymer carrageenan," Carbon, vol. 50, Issue 3, Mar. 2012, pp. 1197-1208.
Aldalbahi, Ali, "Nano-composite materials from carrageenan, conducting polymers and carbon nanotubes," Doctor of Philosophy Thesis, School of Chemistry, University of Wollongong, 2012.

\* cited by examiner

FIG. 16 ated carbon nanotubes, which displays significant strength, heat dispersal, and electrical properties. Buckypaper is generally synthesized by mixing carbon nanotubes with a surfactant to improve dispersability of the carbon nanotubes and overcome their high surface potential and Van der waals force. The dispersed nanoparticles are then aggregated into buckypaper by techniques such as vacuum filtration. One drawback of this approach is the need to then remove the surfactant from the buckypaper, which can be difficult to accomplish and increases the cost of production significantly.

BIO BUCKYPAPER SYNTHESIZED WITH FISH SCALES

BACKGROUND

1. Field

The disclosure of the present patent application relates to nanotechnology, and particularly to a bio buckypaper synthesized with fish scales.

2. Description of the Related Art

Carbon nanotubes are subject of significant investigation due to their unique electronic, mechanical, and thermal properties. Carbon nanotubes are cylindrically structured carbon allotropes. Carbon nanotubes may be single-walled or multi-walled, depending upon the number of layers of graphene present in the carbon nanotube. In use, carbon nanotubes are often formed into more complex structures, such as buckypaper. Buckypaper is a thin sheet of aggregated carbon nanotubes, which displays significant strength, heat dispersal, and electrical properties. Buckypaper is generally synthesized by mixing carbon nanotubes with a surfactant to improve dispersability of the carbon nanotubes and overcome their high surface potential and Van der waals force. The dispersed nanoparticles are then aggregated into buckypaper by techniques such as vacuum filtration. One drawback of this approach is the need to then remove the surfactant from the buckypaper, which can be difficult to accomplish and increases the cost of production significantly.

Thus, a bio buckypaper synthesized with fish scales solving the aforementioned problems is desired.

SUMMARY

A bio buckypaper synthesized with fish scales may be manufactured by mixing carrageenan with a bio waste solution to provide a first mixture, adding carbon nanotubes to the first mixture produce a second mixture, sonicating the second mixture, and evaporative-casting the second mixture to produce the bio buckypaper. In an embodiment, the carrageenan may be T-carrageenan. In an embodiment, the carbon nanotubes may be single walled carbon nanotubes (SWCNTs) or multi-walled carbon nanotubes (MWCNTs). In an embodiment, the bio waste solution may be derived from fish scales.

In an embodiment, the bio buckypaper includes a buckypaper having carbon nanotubes, carrageenan, and fish scales.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A bio buckypaper synthesized with fish scales may be manufactured by mixing carrageenan with a bio waste solution to provide a first mixture, adding carbon nanotubes to the first mixture to produce a second mixture, sonicating the second mixture, and evaporative-casting the second mixture to produce the bio buckypaper. In an embodiment, the carrageenan may be τ-carrageenan. In an embodiment, the carbon nanotubes may be single walled carbon nanotubes or multi-walled carbon nanotubes.

As used herein, the term "about," when used to modify a numerical value, means within ten percent of that numerical value.

In an embodiment, the bio buckypaper includes a buckypaper having carbon nanotubes, carrageenan, and fish scales.

Fish scales are a bio waste material produced when fish are prepared for human consumption. One object of this invention is to recycle bio waste to reduce the impact of landfills or other bio waste disposal mechanisms on the environment. The bio waste may be derived from fish scales. The fish scales may be waste fish scales. In an embodiment, the bio waste may be in an amount ranging from about 30 mg to about 75 mg powdered fish scales. The powdered fish scales may be suspended in a boiling solution of about 15 ml to about 50 ml ethanol and deionized water (1:9 v/v), to produce the bio waste solution.

Carrageenan is a biopolymer commonly extracted from Rhodophyta (red seaweed). There are three main types of carrageenan, Kappa-carrageenan, iota-carrageenan, and lambda-carrageenan. These types of carrageenan are distinguished by their degree of sulfation. Kappa-carrageenan has a single sulfate group per disaccharide, while iota-carrageenan has two, and lambda-carrageenan has three. In an embodiment, the carrageenan may be iota carrageenan. In a further embodiment the iota carrageenan may be τ-carrageenan.

In an embodiment, the CNTs may be added to produce a final carbon nanotube concentration of about 0.1% w/v in the mixture.

The following examples illustrate the present teachings.

Example 1

Preparation of Bio Buckypaper

A bio waste solution was prepared by mixing ethanol and deionized water (1:9 v/v) (15-50 ml total volume), boiling, and adding between about 30 mg and about 75 mg powdered fish scales to the mixture to produce the bio waste solution. About 120 mg τ-carrageenan (IC) was then added to about 15 ml of the bio waste solution and stirred for about 3 hours at about 70° C. to produce a biopolymer/bio waste mixture. SWCNTs (15 mg) or MWCNTs (10 mg) were then added to the biopolymer/bio waste mixture, and the resulting CNTs/carrageenan/bio waste mixtures were sonicated with a digital sonicator with a probe diameter of 10 mm, in pulse mode (0.5 s on/off), ultrasonic power of 750 W, and a frequency of 20 kHz. During sonication, the mixtures were maintained at constant temperature by placing them in 20° C. water baths. The mixtures were then used to prepare bio buckypapers by evaporative-casting in petri dishes and drying in the oven at 35° C. for about 24 hours.

Example 2

Analysis of Bio Buckypapers

Figure 1:
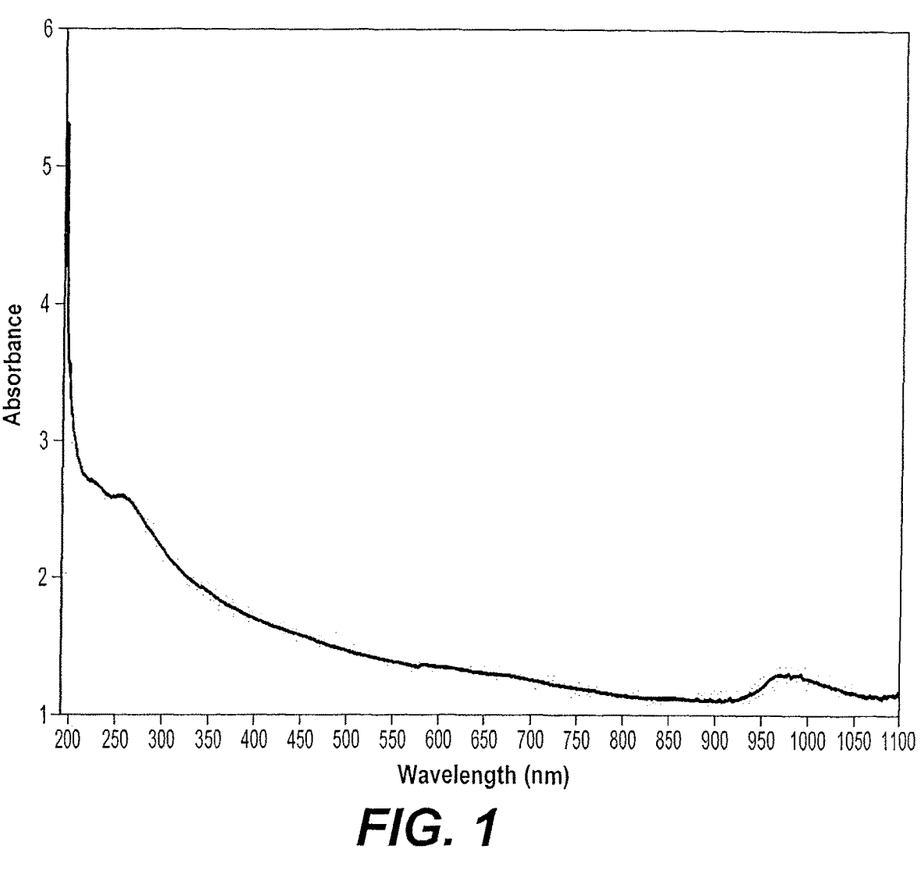
FIG. 1 depicts an ultraviolet spectrum of bio buckypaper synthesized using MWCNTs.
Figure 2:
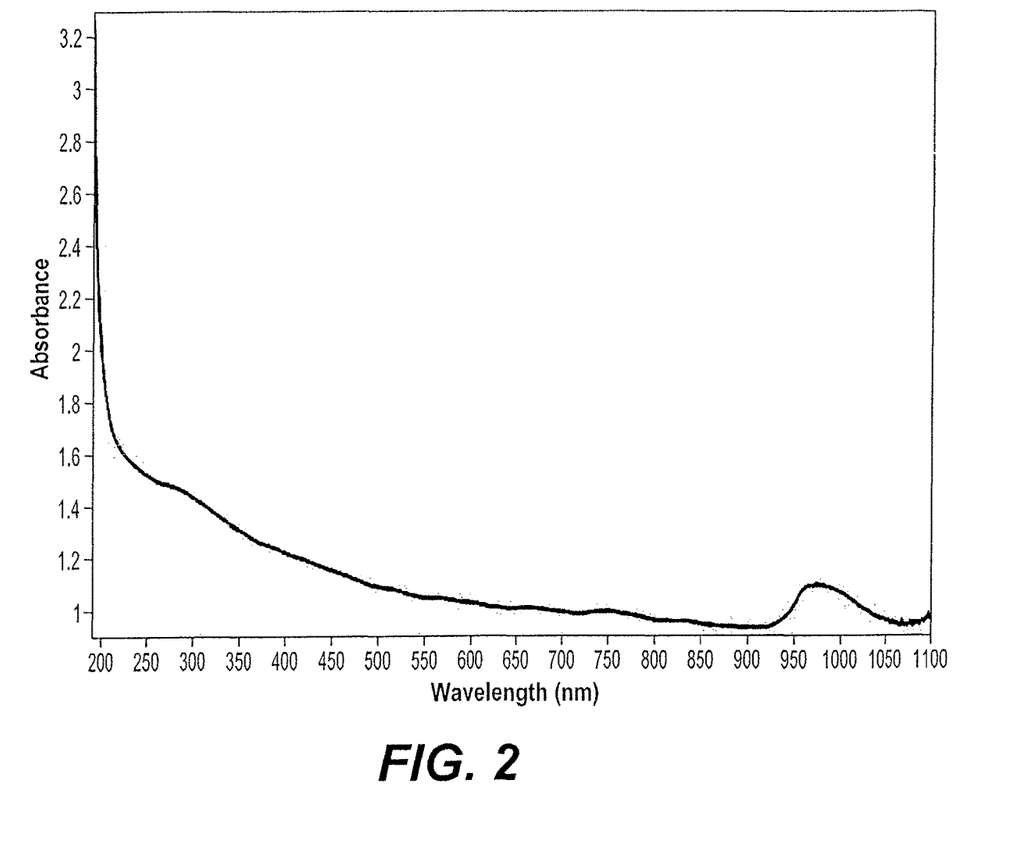
FIG. 2 depicts an ultraviolet spectrum of bio buckypaper synthesized using SWCNTs.

Bio buckypapers prepared according to the method of Example 1 with both SWCNTs and MWCNTs were analyzed. The ultraviolet-visible-absorption spectrum of bio buckypaper synthesized with MWCNTs demonstrated an absorption peak at 200-250 nm (FIG. 1), while the spectrum of bio buckypaper synthesized with SWCNTs had an absorption peak at 250-300 nm and illustrated absorbance of dispersed CNTs at 600-660 nm (the maximum absorption band arising from van Hove singularities for SWNTs).

Figure 3:
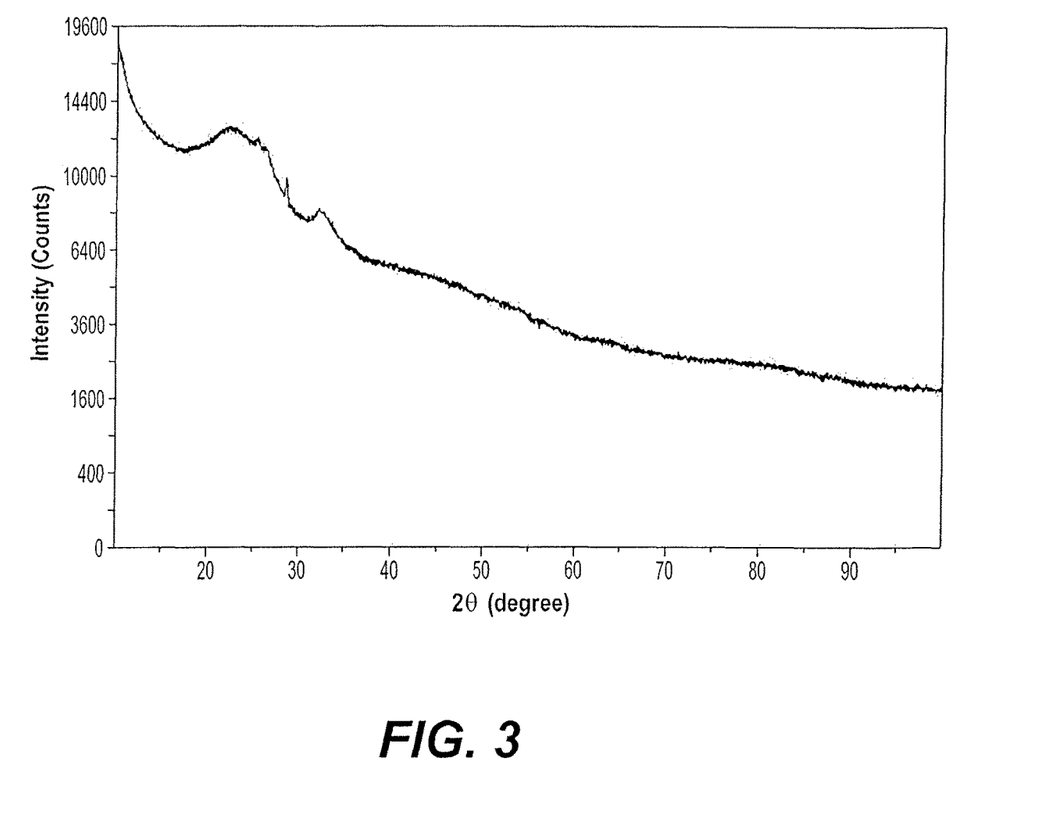
FIG. 3 depicts a X-ray diffraction spectrum of bio buckypaper synthesized using MWCNTs.
Figure 4:
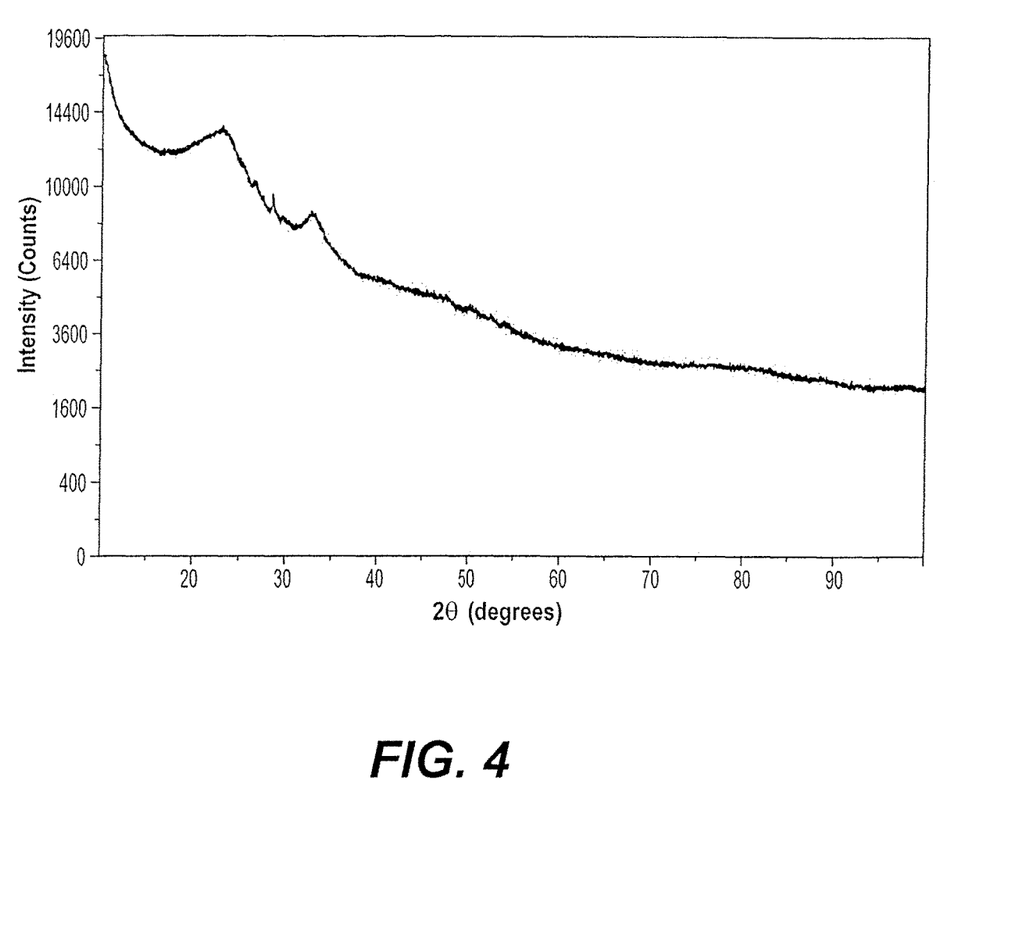
FIG. 4 depicts a X-ray diffraction spectrum of bio buckypaper synthesized using SWCNTs.
Figure 5A:
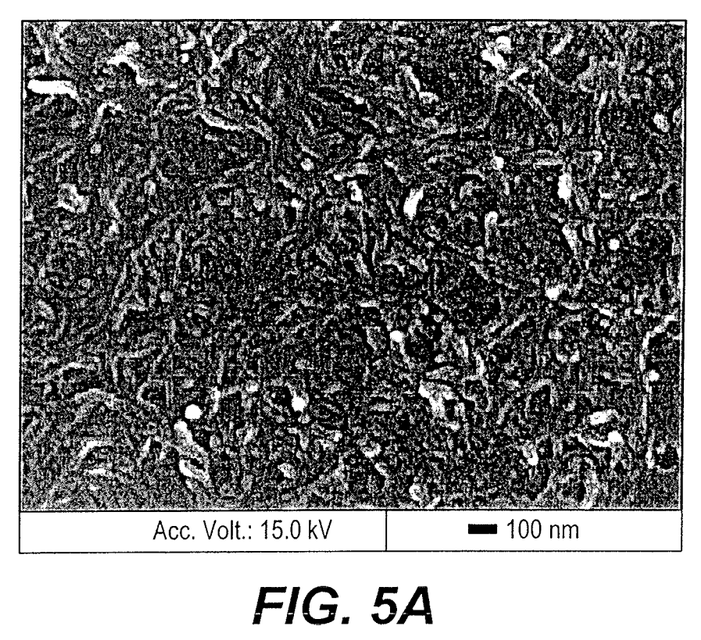
FIG. 5A depicts a scanning electron micrograph spectrum of bio buckypaper synthesized using MWCNTs.
Figure 5B:
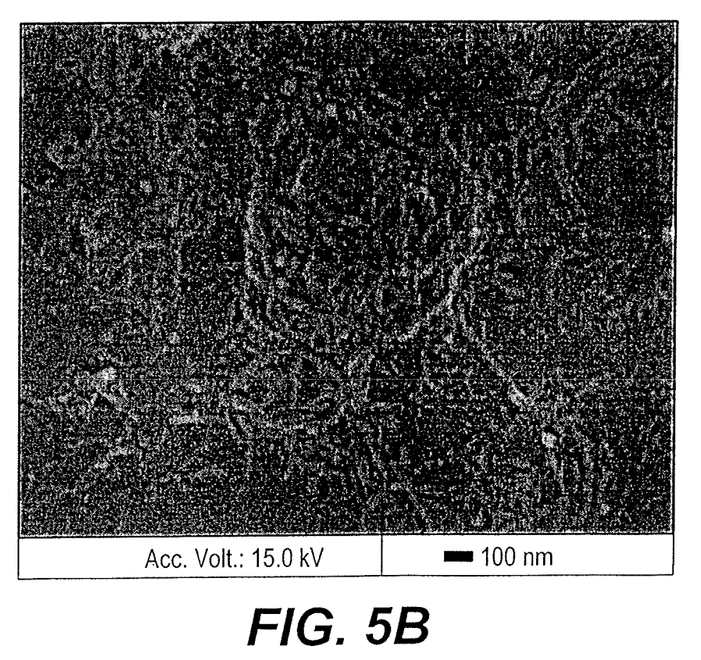
FIG. 5B depicts a scanning electron micrograph spectrum of bio buckypaper synthesized using MWCNTs.
Figure 6A:
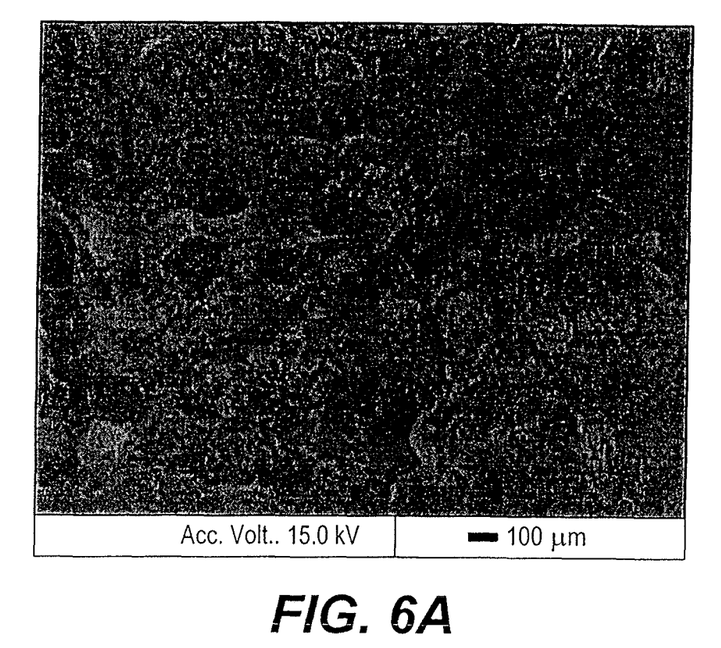
FIG. 6A depicts a scanning electron micrograph spectrum of bio buckypaper synthesized using SWCNTs.
Figure 6B:
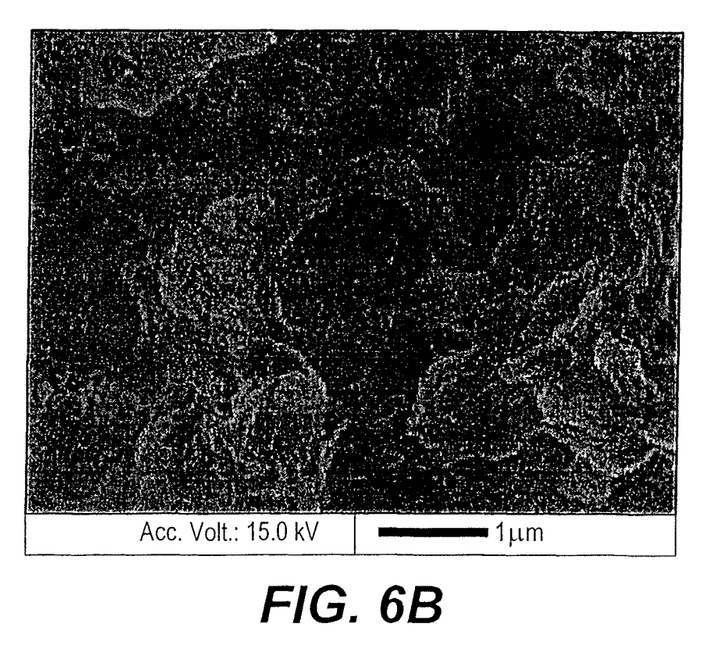
FIG. 6B depicts a scanning electron micrograph spectrum of bio buckypaper synthesized using SWCNTs.
Figure 7A:
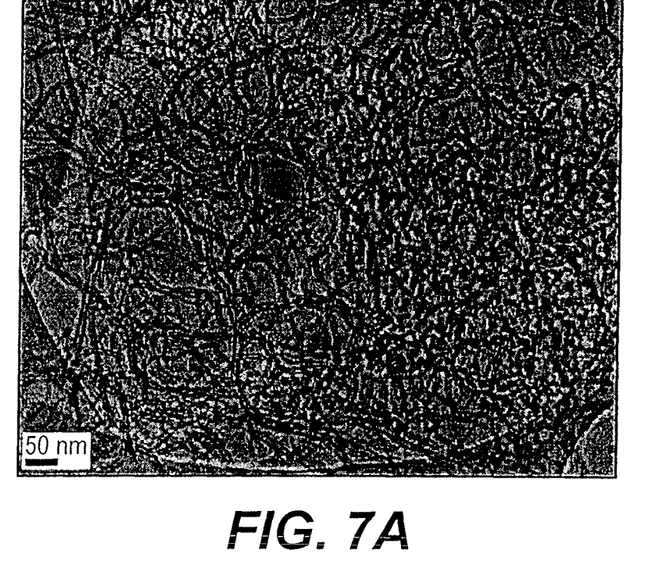
FIG. 7A depicts a transmission electron micrograph spectrum of bio buckypaper synthesized using MWCNTs.
Figure 7B:
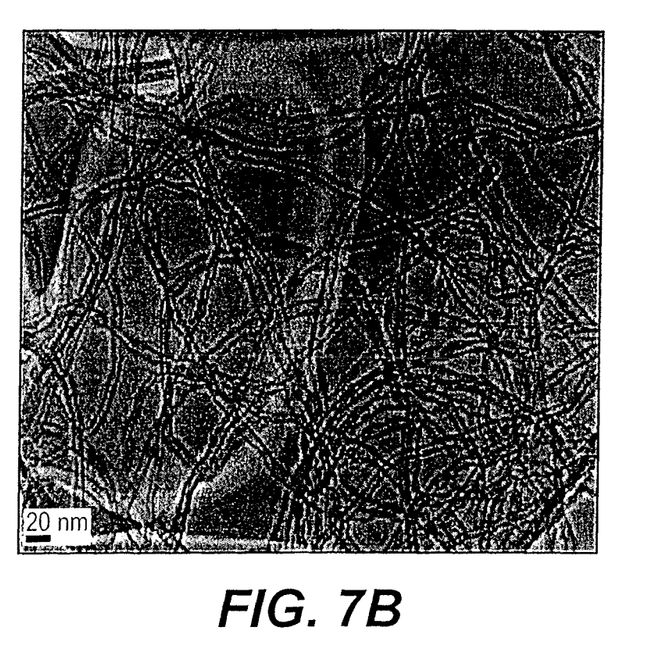
FIG. 7B depicts a transmission electron micrograph spectrum of bio buckypaper synthesized using MWCNTs.
Figure 8A:
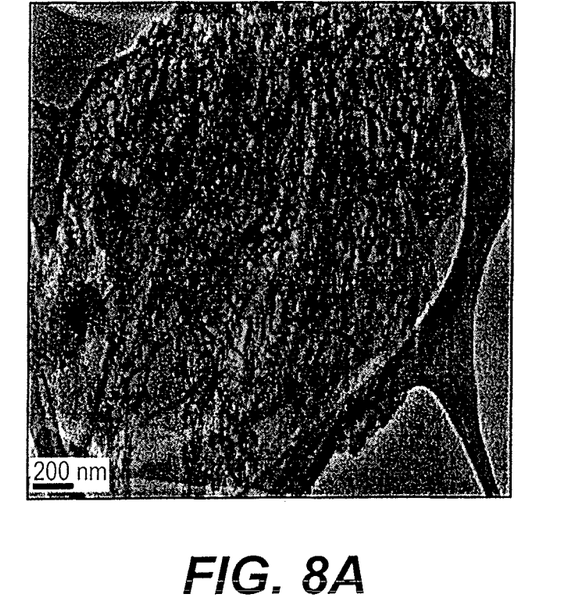
FIG. 8A depicts a transmission electron micrograph spectrum of bio buckypaper synthesized using SWCNTs.
Figure 8B:
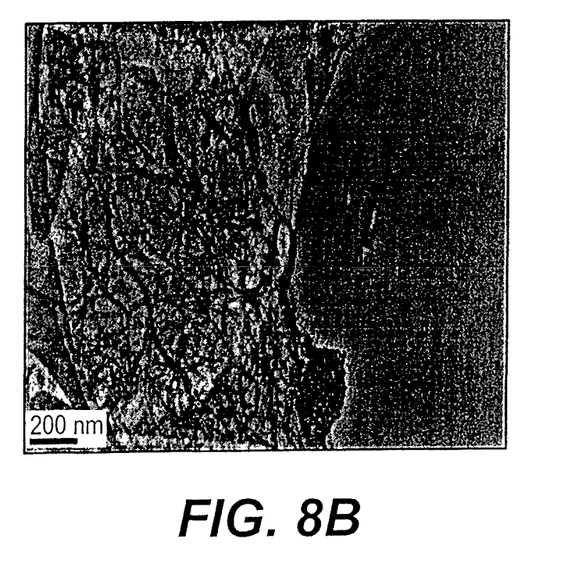
FIG. 8B depicts a transmission electron micrograph spectrum of bio buckypaper synthesized using SWCNTs.

An X-ray diffraction spectrum of bio buckypaper synthesized with MWCNTs illustrated characteristic MWNCT peaks at 2θ angle and about 26° (FIG. 3). An X-ray diffraction spectrum of bio buckypaper synthesized with SWCNTs illustrated characteristic SWNCT peaks at about 25° (FIG. 4). CNT reinforced polymer peaks are shifted to about 20° and about 30°, respectively (See FIGS. 3 and 4). The peak shift and reduced X-ray intensity further support the formation of a nanocomposite.

Scanning electron micrographs of bio buckypapers synthesized with MWCNTs and SWCNTs, respectively, demonstrate polymer aggregation of composite biopolymer τ-carrageenan, fish scales, and CNTs (FIGS. 5A-5B and FIGS. 6A-6B).

Transmission electron micrographs of bio buckypapers synthesized with MWCNTs and SWCNTs, respectively, demonstrate CNTs reinforced in a polymer matrix (FIGS. 7A-7B and FIGS. 8A-8B).

Figure 9:
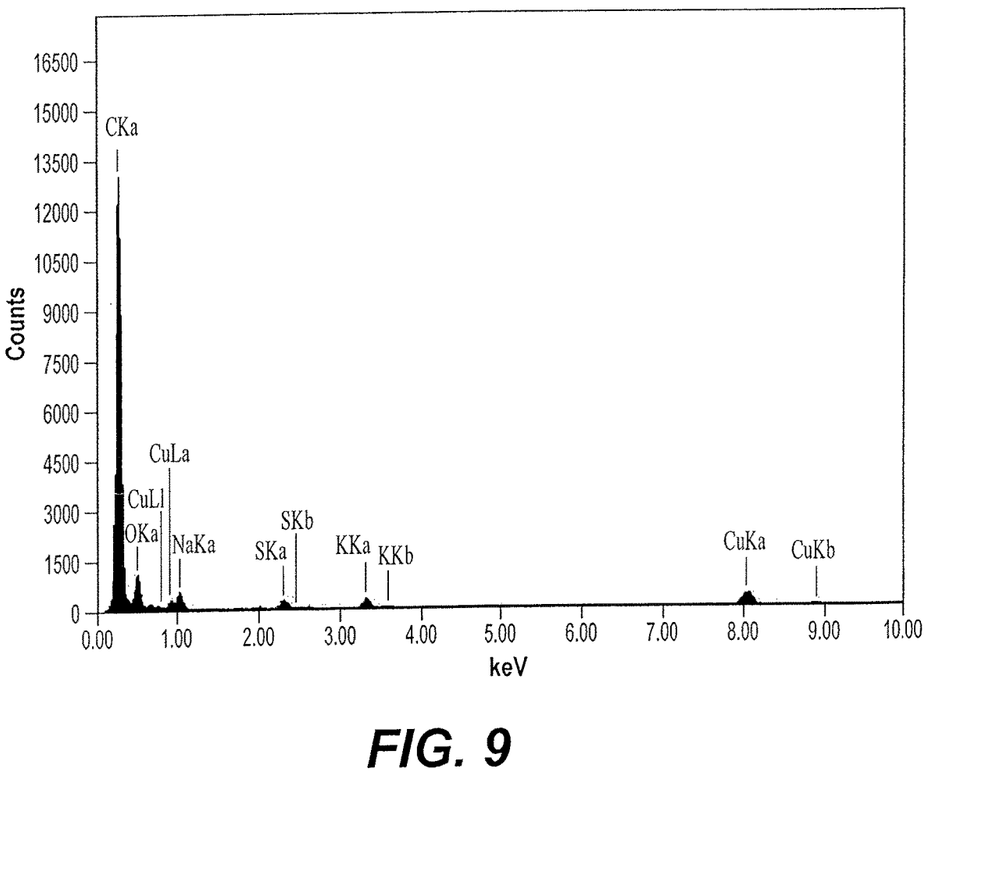
FIG. 9 depicts an energy dispersive X-ray spectrum of bio buckypaper synthesized using MWCNTs.
Figure 10:
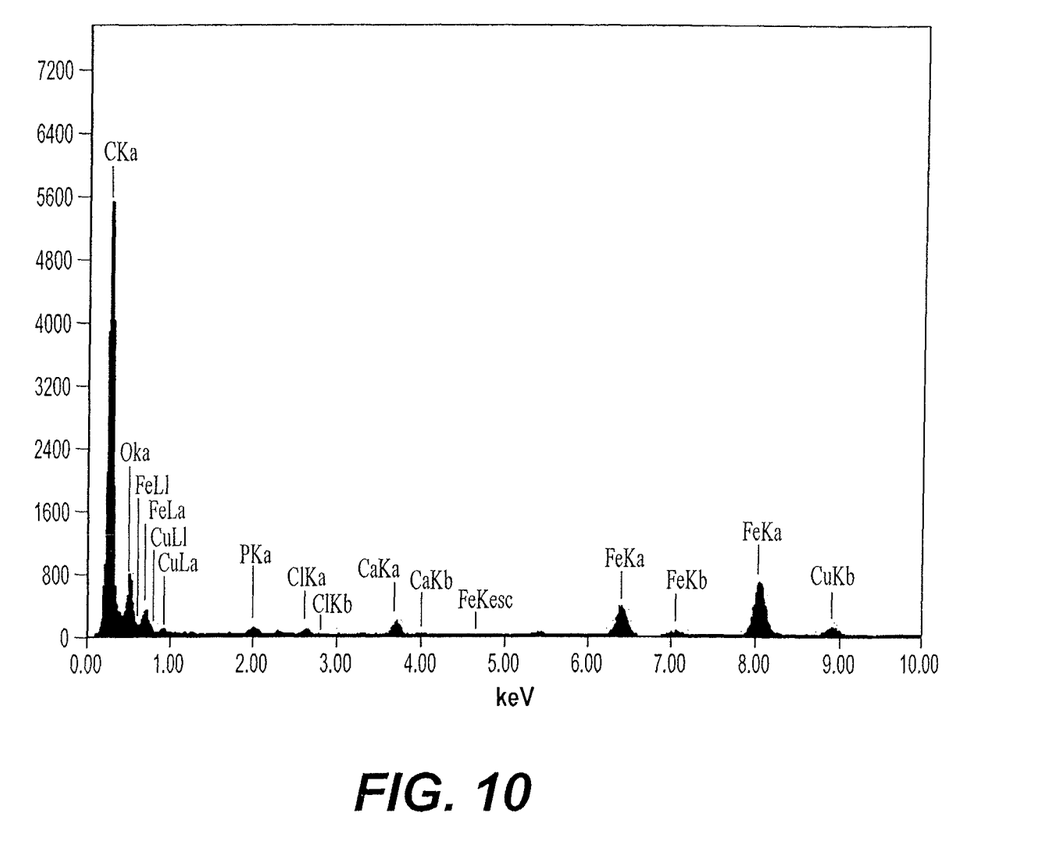
FIG. 10 depicts an energy dispersive X-ray spectrum of bio buckypaper synthesized using SWCNTs.

Energy-dispersive X-ray spectroscopy (Oxford Instrument, Incax-act, UK) using a JEM-21000F transmission electron microscope of bio buckypapers synthesized with MWCNTs and SWCNTs revealed strong signals for carbon and oxygen, and confirmed the presence of other elements, such as Cu, Fe, P, S, Ca, and K (FIGS. 9-10).

Figure 11:
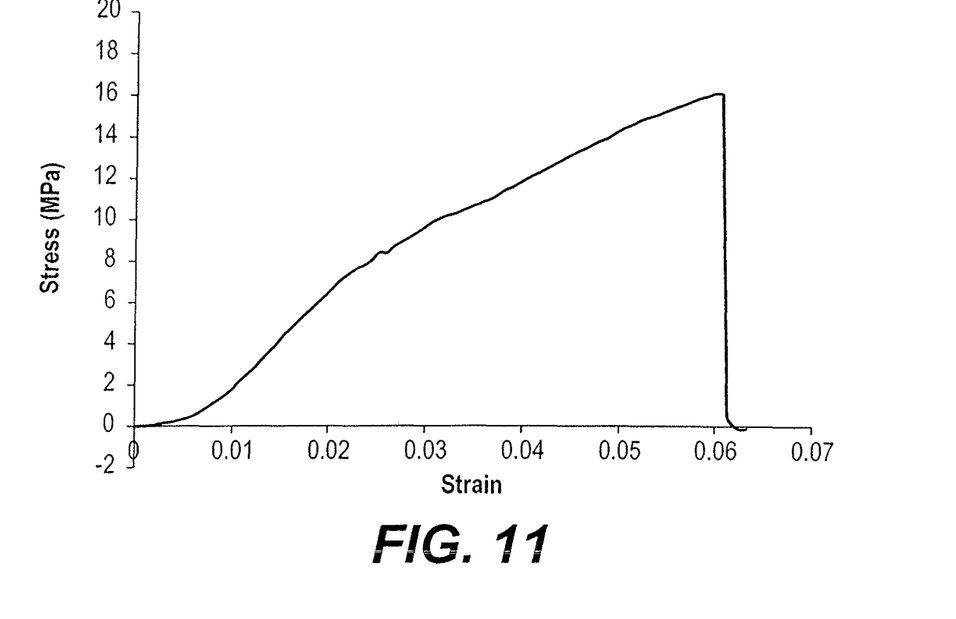
FIG. 11 depicts a graph of tensile testing stress versus strain curves for bio buckypaper synthesized using SWCNTs
Figure 12:
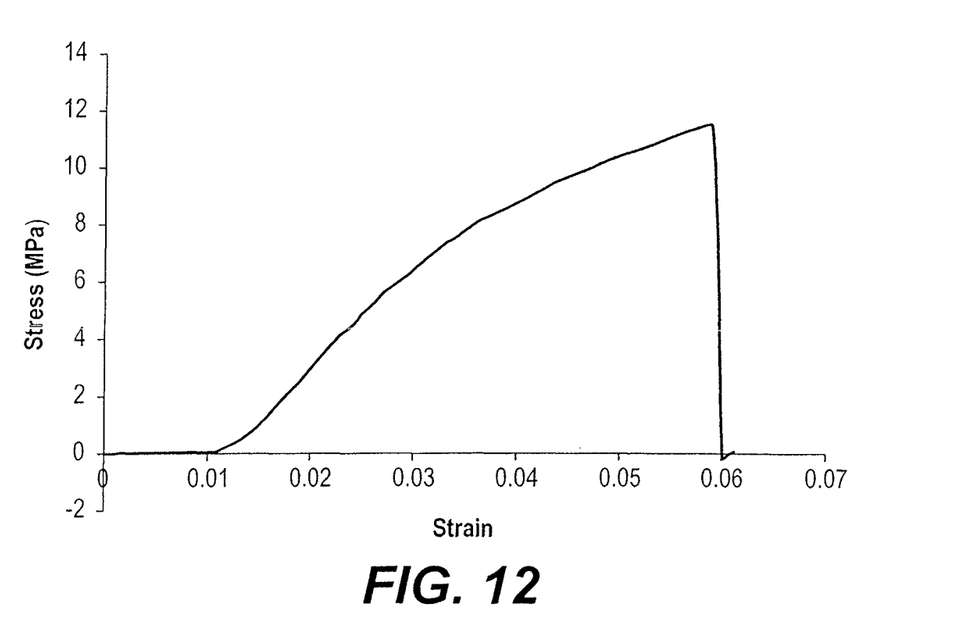
FIG. 12 depicts a graph of tensile testing stress versus strain curves for bio buckypaper synthesized using MWCNTs

The mechanical properties of the bio buckypapers synthesized using MWCNTs and SWCNTs, respectively, were analyzed using a dynamic mechanical analyzer (Q800; TA instruments, New Castle, Del., USA). The bio buckypaper synthesized with SWCNTs exhibited a tensile strength at about 12 MPa (FIG. 11). The bio buckypaper synthesized with MWCNTs exhibited a tensile strength at about 16 MPa (FIG. 12). Thus, the incorporation of CNTs in the biopolymer matrix appears to have had a reinforcement effect, increasing the tensile strength of the bio buckypapers.

Figure 13:
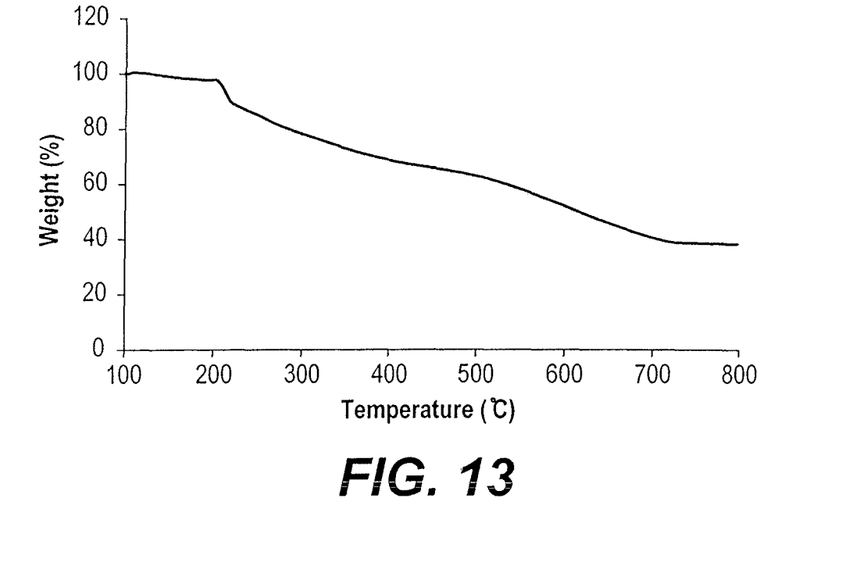
FIG. 13 depicts a thermogravimetric analysis thermogram of bio buckypaper synthesized using SWCNTs.
Figure 14:
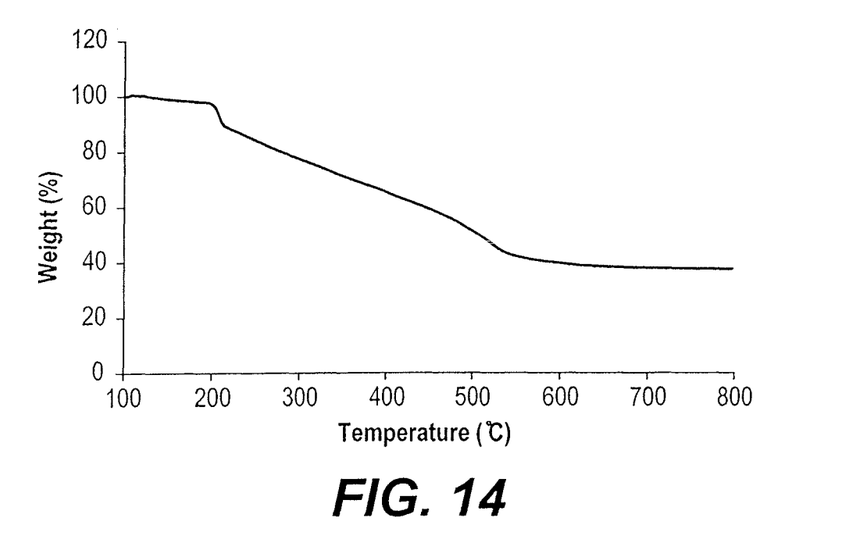
FIG. 14 depicts a thermogravimetric analysis thermogram of bio buckypaper synthesized using MWCNTs.

Thermo-gravimetric analysis profiles of the bio buckypapers were recorded from 100° C. to 800° C. in a nitrogen atmosphere (FIGS. 12-13). Degradation was not observed between 100° C. and 200° C. Degradation occurred between 200° C. and 700° C., resulting in about 62% overall weight loss (FIGS. 12-13). This suggests the bio buckypapers synthesized according to the method of Example 1 have improved thermal stability.

Figure 15:
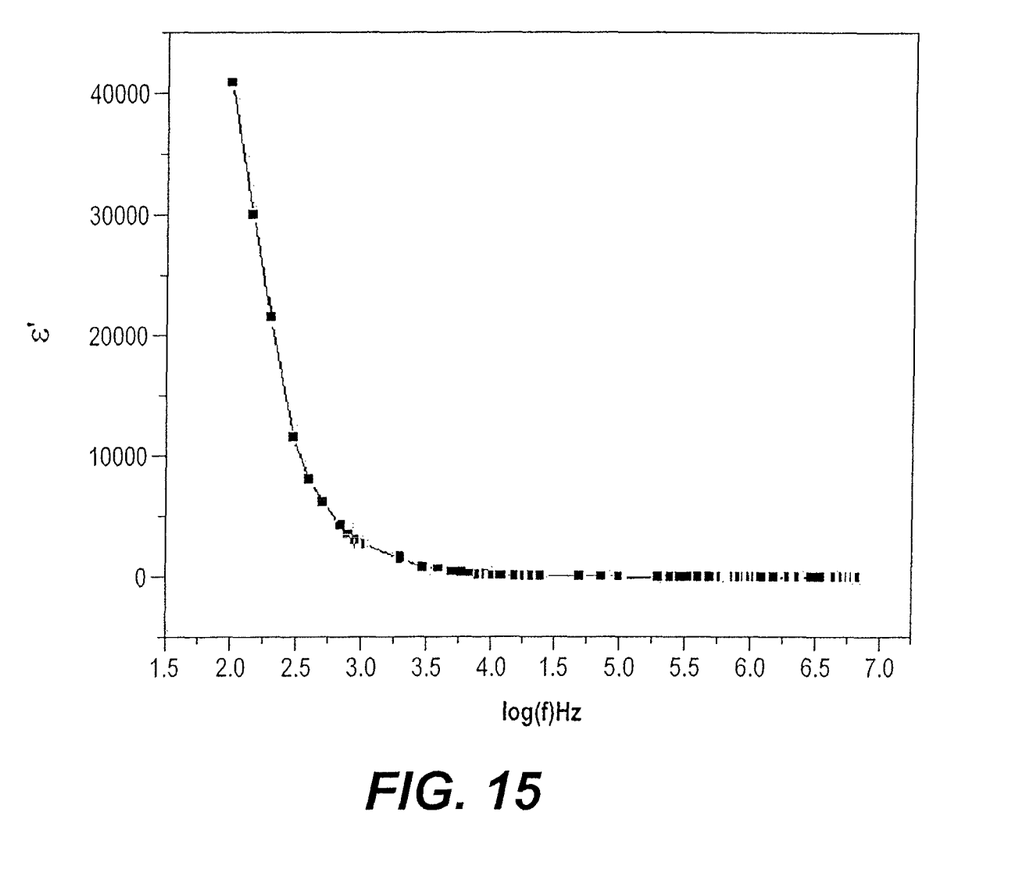
FIG. 15 depicts a graph of the dielectric constant as a function of applied frequency for bio buckypaper synthesized with SWCNTs.
Figure 16:
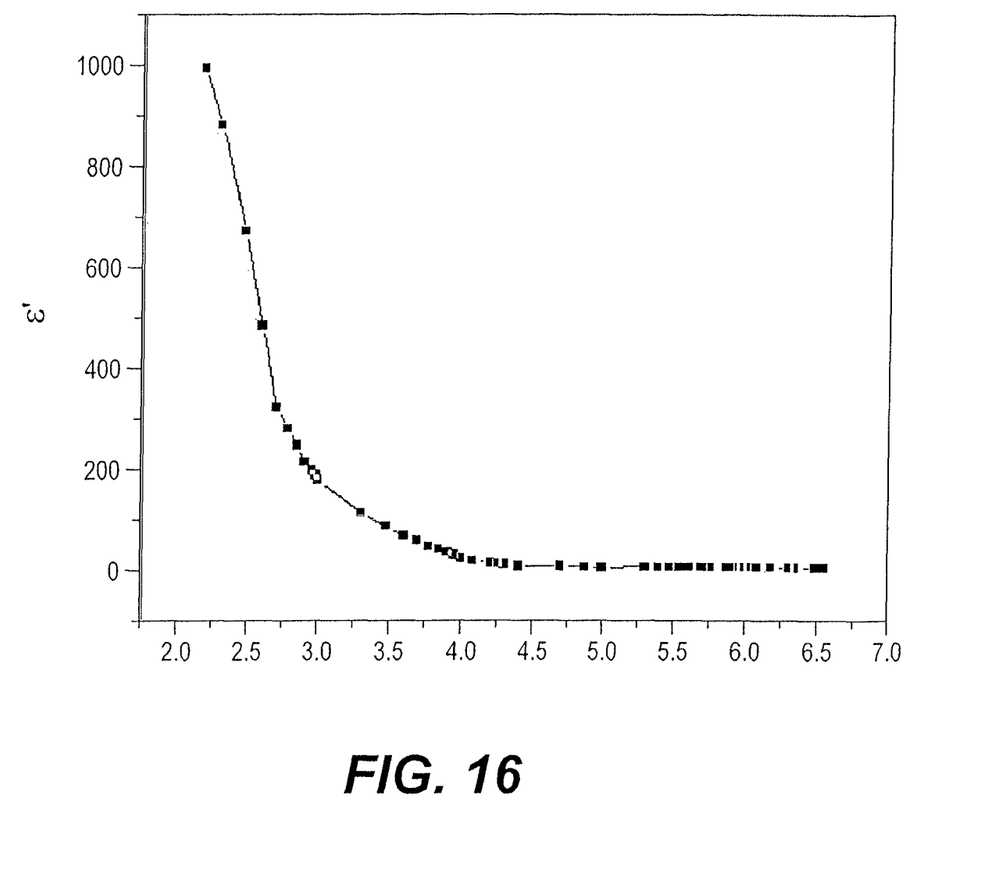
FIG. 16 depicts a graph of the dielectric constant as a function of applied frequency for bio buckypaper synthesized with MWCNTs.

Dielectric properties of the bio buckypapers were measured and the dielectric constant was graphed as a function of applied frequency (FIGS. 15-16). Both bio buckypapers tested showed notably high dielectric constants at low frequency. This may indicate the presence of space charge effects. At higher frequencies, the dielectric constants were relatively constant.

It is to be understood that the method of synthesis of bio buckypaper is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of synthesis of bio buckypaper, comprising:
synthesizing a bio waste solution from fish scales, wherein the bio waste solution is synthesized by adding about 30 mg to about 75 mg powdered fish scales into a boiling solution of about 15 ml to about 50 ml ethanol and deionized water (1:9 v/v);
mixing a carrageenan with the bio waste solution to provide a first mixture;
adding carbon nanotubes to the first mixture to produce a second mixture;
sonicating the second mixture; and
evaporative-casting the second mixture to produce bio buckypaper.

2. The method of synthesis of bio buckypaper according to claim 1, wherein the carrageenan comprises iota-carrageenan.

3. The method of synthesis of bio buckypaper according to claim 2, wherein the iota-carrageenan comprises τ-carrageenan.

4. The method of synthesis of bio buckypaper according to claim 1, wherein about 120 mg of the carrageenan is mixed with about 15 ml of the bio waste solution.

5. The method of synthesis of bio buckypaper according to claim 1, wherein the carrageenan is mixed with the bio waste solution by stirring for 3 hours at about 70° C.

6. The method of synthesis of bio buckypaper according to claim 1, wherein the carbon nanotubes are single walled carbon nanotubes.

7. The method of synthesis of bio buckypaper according to claim 6, wherein about 15 mg of the carbon nanotubes is added to the first mixture.

8. The method of synthesis of bio buckypaper according to claim 1, wherein the carbon nanotubes are multi-walled carbon nanotubes.

9. The method of synthesis of bio buckypaper according to claim 8, wherein about 10 mg of the carbon nanotubes is added to the first mixture.

\* \* \* \* \*